United States Patent [19]
Johnson et al.

[11] Patent Number: 5,896,579
[45] Date of Patent: Apr. 27, 1999

[54] WELDING HELMET WITH AIR CIRCULATING SYSTEM

[76] Inventors: Bennett Johnson; Dresden Johnson, both of 2637 Kavalier Dr., Palm Harbor, Fla. 34684

[21] Appl. No.: 08/942,057

[22] Filed: Oct. 1, 1997

[51] Int. Cl.⁶ ........................................ A61F 9/06
[52] U.S. Cl. ............................................. 2/8; 2/7
[58] Field of Search .................... 2/8, 171.3, 7, 422

[56] References Cited

U.S. PATENT DOCUMENTS

| | | | |
|---|---|---|---|
| 4,172,294 | 10/1979 | Harris | 2/8 |
| 4,309,774 | 1/1982 | Guzowski | 2/8 |
| 4,890,335 | 1/1990 | Crowson | 2/8 |
| 5,123,114 | 6/1992 | Desanti | 2/8 |
| 5,353,605 | 10/1994 | Naaman | 2/171.3 |
| 5,561,855 | 10/1996 | McFall | 2/8 |

*Primary Examiner*—Michael A. Neas
*Attorney, Agent, or Firm*—Joseph N. Breaux

[57] ABSTRACT

A welding helmet with an air circulating system that includes a welding hood, a head band assembly, and an air circulating system. The welding hood has an interior face receiving cavity defined by an interior helmet surface. The head band assembly being pivotally mounted to the welding helmet. The air circulating system including an air circulating assembly mounted to a top portion of the welding hood, a cooling water storage bottle attached to a back portion of the head band, a wick conduit connected between the air circulating assembly and the cooling water storage bottle, a detachable battery pack housing mountable to a front structure of the air cooling assembly, and a pivotally actuated air circulating assembly on/off switch mounted between the welding hood and the head band.

19 Claims, 3 Drawing Sheets

5,896,579

WELDING HELMET WITH AIR CIRCULATING SYSTEM

TECHNICAL FIELD

The present invention relates to protective equipment and more particularly to a protective welding helmet that includes an air circulating system for circulating filtered and cooled air to the head and face area of a welder; the welding helmet with air circulating system including a welding hood, a head band assembly, and an air circulating system; the welding hood has an interior face receiving cavity defined by an interior helmet surface; the head band assembly being pivotally mounted to the welding helmet; the air circulating system including an air circulating assembly mounted to a top portion of the welding hood, a cooling water storage bottle attached to a back portion of the head band, a wick conduit connected between the air circulating assembly and the cooling water storage bottle, a detachable battery pack housing mountable to a front structure of the air cooling assembly, and a pivotally actuated air circulating assembly on/off switch mounted between the welding hood and the head band; the battery pack housing having a battery provided therein and a pair of contact pads on a battery pack exterior surface thereof; the air circulating assembly including the assembly housing mounted to the exterior top portion of the welding hood, a discharge airflow opening formed between an interior airflow chamber of the assembly housing and the interior face receiving cavity of the welding hood, an air circulating fan housed within the airflow chamber of the assembly housing having an electric motor that rotates a number of fan blades to draw air through the airflow chamber intake opening, across an evaporative cooling pad positioned within the airflow chamber, through an activated charcoal filter element positioned within the airflow chamber, and out through the discharge airflow opening into the interior face receiving cavity of the welding hood to provide cool, clean air to a user; the evaporative cooling pad being supplied with water from the cooling water storage bottle by a wick positioned through the wick conduit.

BACKGROUND OF THE INVENTION

Welding is often performed under hot conditions in which the air quality is less than desirable. These poor work conditions are further aggravated by the typical need for the welder to wear a protective welding helmet with a tinted viewing port to protect his/her face and eyes from the intense light, smoke and hot sparks generated during the welding process. It would be a benefit, therefore, for a welder to have a welding helmet that included an air circulating system for circulating air into the welding hood to provide a cooling effect to the welder's face. It would of course be a further benefit to have a welding helmet that includes an air circulating system having a mechanism for cooling the air prior to circulating the air onto the welder's face. It would also be a benefit if the air circulating system included an air filtering mechanism that filtered the air to remove particles and unpleasant odors from the air prior to circulating the air onto the welder's face.

SUMMARY OF THE INVENTION

It is thus an object of the invention to provide a welding helmet with an air circulating system for circulating air onto the face of a welder.

It is a further object of the invention to provide a welding helmet with an air circulating system that has a mechanism for cooling the air prior to circulating the air onto a welder's face.

It is a still further object of the invention to provide a welding helmet with an air circulating system that includes an air filtering mechanism that filters the air to remove particles and unpleasant odors from the air prior to circulating the air onto a welder's face.

It is a still further object of the invention to provide a welding helmet with an air circulating system that includes a welding hood, a head band assembly, and an air circulating system; the welding hood having an interior face receiving cavity defined by an interior helmet surface; the head band assembly being pivotally mounted to the welding helmet; the air circulating system including an air circulating assembly mounted to a top portion of the welding hood, a cooling water storage bottle attached to a back portion of the head band, a wick conduit connected between the air circulating assembly and the cooling water storage bottle, a detachable battery pack housing mountable to a front structure of the air cooling assembly, and a pivotally actuated air circulating assembly on/off switch mounted between the welding hood and the head band; the battery pack housing having a battery provided therein and a pair of contact pads on a battery pack exterior surface thereof; the air circulating assembly including: an assembly housing mounted to the exterior top portion of the welding hood; a discharge airflow opening formed between an interior airflow chamber of the assembly housing and the interior face receiving cavity of the welding hood; an air circulating fan housed within the airflow chamber of the assembly housing having an electric motor that rotates a number of fan blades to draw air through the airflow chamber intake opening, across an evaporative cooling pad positioned within the airflow chamber, through an activated charcoal filter element positioned within the airflow chamber, and out through the discharge airflow opening into the interior face receiving cavity of the welding hood to provide cool), clean air to a user; the evaporative cooling pad being a fibrous pad supplied with water from the cooling water storage bottle by a wick positioned through the wick conduit. The filter element is preferably removable through a pivotable top member of the assembly housing.

It is a still further object of the invention to provide a welding helmet with an air circulating system that accomplishes some or all of the above objects in combination.

Accordingly, a welding helmet with an air circulating system is provided. The welding helmet with an air circulating system includes a welding hood, a head band assembly, and an air circulating system; the welding hood having an interior face receiving cavity defined by an interior helmet surface; the head band assembly being pivotally mounted to the welding helmet; the air circulating system including an air circulating assembly mounted to a top portion of the welding hood, a cooling water storage bottle attached to a back portion of the head band, a wick conduit connected between the air circulating assembly and the cooling water storage bottle, a detachable battery pack housing mountable to a front structure of the air cooling assembly, and a pivotally actuated air circulating assembly on/off switch mounted between toe welding hood and the head band; the battery pack housing having a battery provided therein and a pair of contact pads on a battery pack exterior surface thereof; the air circulating assembly including: an assembly housing mounted to the exterior top portion of the welding hood; a discharge airflow opening formed between an interior airflow chamber of the assembly housing and the interior face receiving cavity of the welding hood; an air circulating fan housed within the airflow chamber of the assembly housing having an electric motor that rotates a number of fan blades to draw air through the airflow chamber intake opening, across an evaporative cooling pad positioned within the airflow chamber, through an activated charcoal filter element positioned within the airflow chamber, and out through the discharge airflow opening into the interior face receiving cavity of the welding hood to provide cool, clean air to a user; the evaporative cooling pad being a fibrous pad supplied with water from the cooling water storage bottle by a wick positioned through the wick conduit. The filter element is preferably removable through a pivotable top member of the assembly housing.

BRIEF DESCRIPTION OF DRAWINGS

For a further understanding of the nature and objects of the present invention, reference should be made to the following detailed description, taken in conjunction with the accompanying drawings, in which like elements are given the same or analogous reference numbers and wherein.

DESCRIPTION OF THE EXEMPLARY EMBODIMENT

Figure 1:
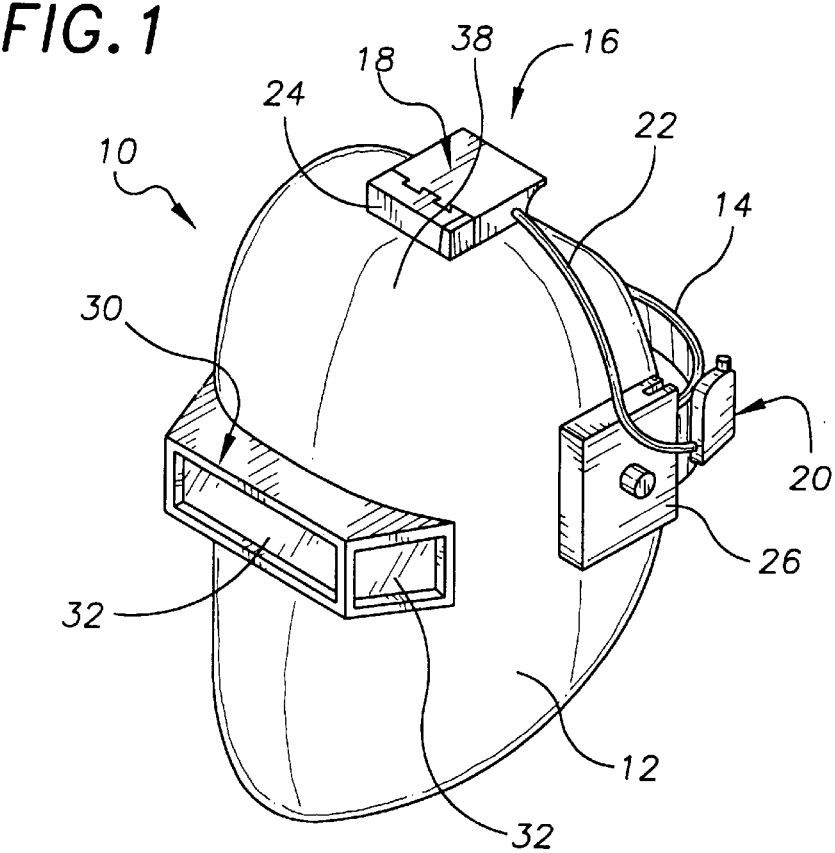
FIG. 1 is a perspective view of an exemplary embodiment of the welding helmet with air circulating system of the present invention showing an exemplary welding hood and head band assembly; and an exemplary air circulating system including the air circulating assembly mounted to the top portion of the welding hood, the cooling water storage bottle attached to the back portion of the head band, the wick conduit connected between the air circulating assembly and the cooling water storage bottle, the detachable battery pack housing mounted to the front of the air cooling assembly, and the pivotally actuated air circulating assembly on/off switch mounted between the welding hood and the head band.

FIG. 1 shows an exemplary embodiment of the welding helmet with air circulating system of the present invention generally designated by the numeral 10. In this embodiment welding helmet with air circulating system 10 includes a molded welding hood 12, a head band assembly 14; and an air circulating system, generally designated 16, that includes an air circulating assembly 18, a cooling water storage bottle 20, a wick conduit 22, a detachable battery pack housing 24, and a pivotally actuated air circulating assembly on/off switch 26. Welding hood 12 is of stamped metal construction and includes a viewing portal, generally designated 30, having three darkly tinted viewing lenses 32 (only two shown). Head band assembly 14 is constructed of molded plastic and is adjustable to fit securely onto the head of the user with a conventional size adjustment mechanism. In this embodiment, air circulating assembly 18 is mounted to a top portion 38 of welding hood 12; cooling water storage bottle 20 is attached to a back portion of head band 14; and wick conduit 22 is connected between air circulating assembly 18 and cooling water storage bottle 20.

Figure 2:
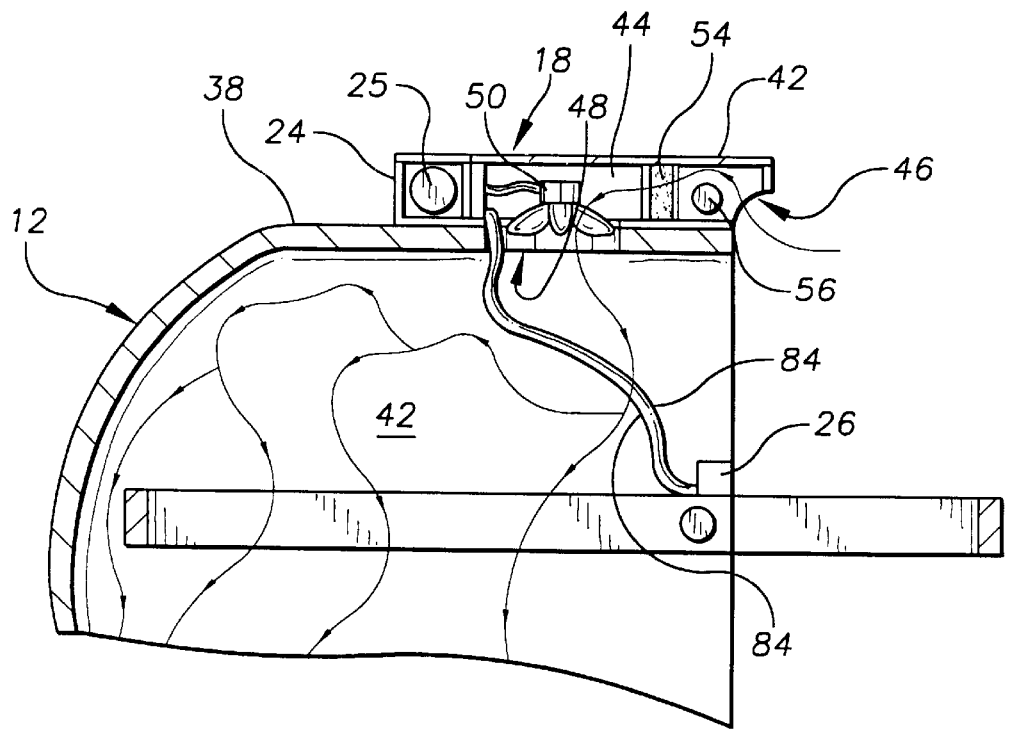
FIG. 2 is a partial cross sectional view of a second exemplary welding helmet with air circulating system showing an interior area of the face receiving cavity of the welding hood, a section of the head band assembly pivotally mounted to the interior wall of the welding helmet; a cross sectional view of the detachable battery pack housing showing a battery housed within a battery compartment formed therein; and a cross sectional view of the air circulating assembly showing the assembly housing mounted to the exterior top portion of the welding hood, the discharge airflow opening between the interior airflow chamber of the assembly housing and the interior of the welding hood, the air circulating fan housed within the airflow chamber of the assembly housing having an electric motor that rotates a number of fan blades to draw air through the airflow chamber intake opening, across the wick supplied evaporative cooling pad, through the activated charcoal filter element and out through the discharge airflow opening into the interior area of the face receiving cavity of the welding hood to provide cool, clean air to a user.
Figure 4:
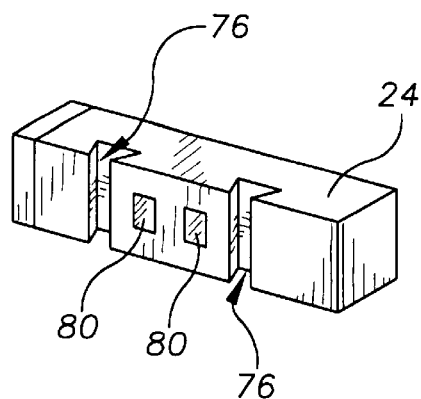
FIG. 4 is a perspective view of the detachable battery pack housing in isolation showing the two rectangular metal battery contact pads positioned between the two parallel attachment channels.
Figure 3:
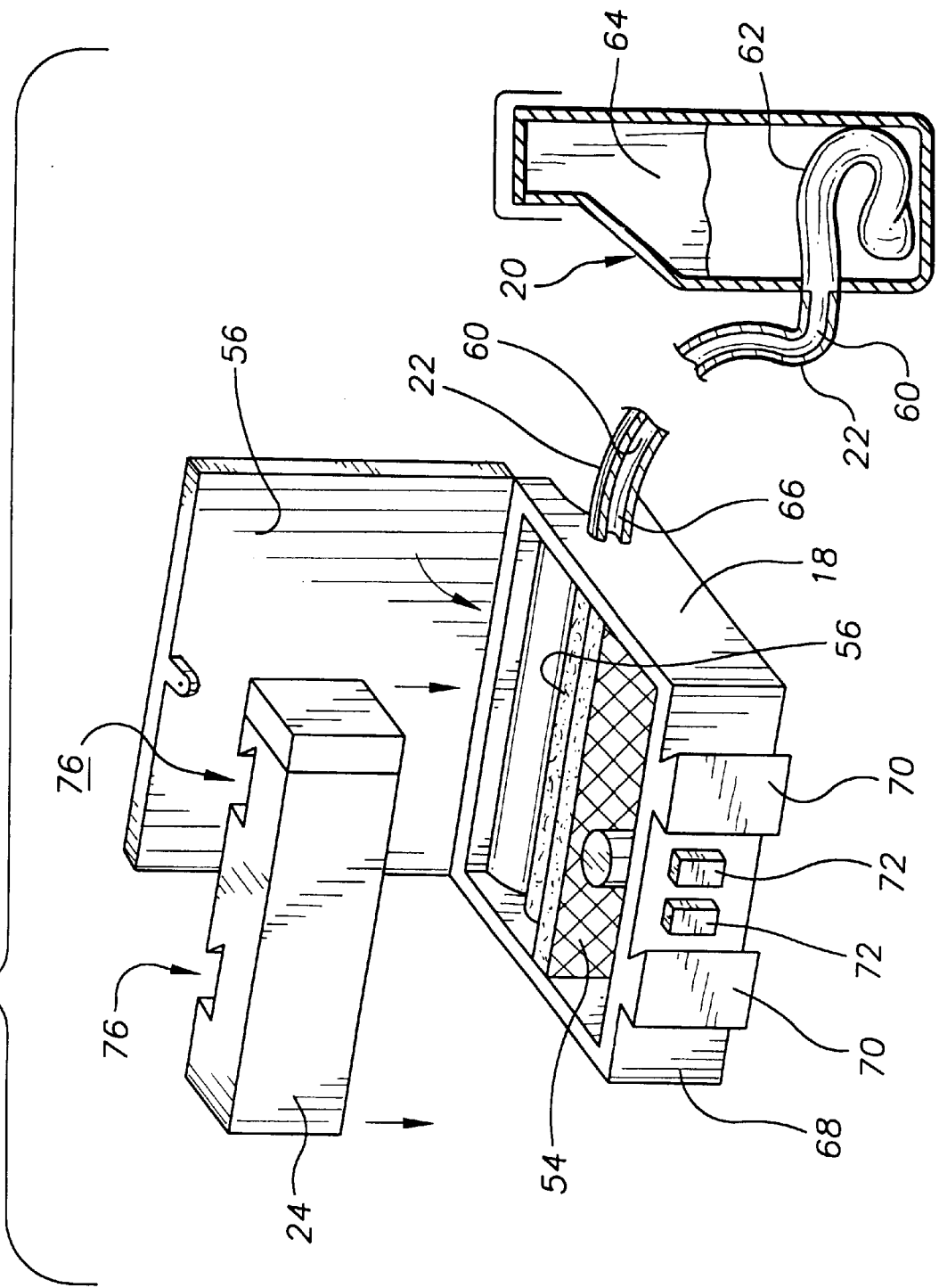
FIG. 3 is a partially exploded cross sectional view of the detachable battery pack housing, the assembly housing of the air circulating assembly with the pivoted into the open position to show the interior airflow chamber, the electric motor of the circulating fan, the wick supplied evaporative cooling pad, the activated charcoal filter element, the wick conduit connected between the assembly housing and the cooling water storage bottle, the absorbent, capillary action wick positioned through the wick conduit into connection between the liquid storage compartment of the cooling water storage bottle and the evaporative cooling pad.

With reference to FIG. 2, welding hood 12 is formed to create an interior face receiving cavity 40 within which the face of the user is positioned during welding. Battery pack housing 24 has a battery compartment formed therein within which a rechargeable battery 25 is positioned. Air circulating assembly 18 includes an assembly housing 42 that has an airflow chamber 44 formed therein in connection between an airflow chamber intake opening 46 and a discharge airflow opening 48; an electric air circulating fan 50 housed within airflow chamber 44 and positioned adjacent to discharge airflow opening 48; an activated charcoal filter element 54; and a cotton evaporative cooling pad 56. With reference now to FIG. 3, assembly housing 18 includes a pivoting top 56 that pivots into an open position to allow insertion of new filter elements 54 when needed. A cotton fiber wick 60 is positioned through wick conduit 22 and has a first end 62 that extends into a water holding chamber 64 formed within cooling water storage bottle 20 and a second end 66 in connection with evaporative cooling pad 56. A front surface 68 of assembly housing 18 has two parallel attachment rails 70 extending outwardly therefrom and two metal electrical contact surfaces 72. Keyways 76 of battery pack housing 24 are shaped to allow insertion thereinto of parallel attachment rails 70 in a manner to secure battery pack housing 24 to assembly housing 18. With reference to FIG. 4, battery pack housing 24 has two rectangular metal battery contact pads 80 in electrical connection with battery 25 (FIG. 2) and that are positioned in relation to keyways 76 so as to make electrical contact with two metal electrical contact surfaces 72 of assembly housing 18 (FIG. 3).

Figure 5:
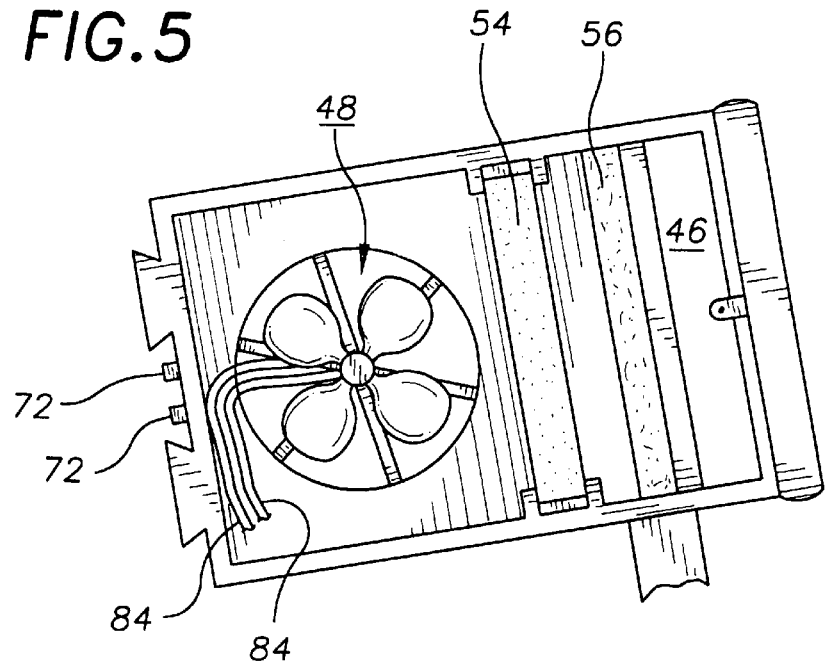
FIG. 5 is a top plan view of the air circulating assembly with the top of the assembly housing pivoted into the open position to show the discharge airflow opening formed through the bottom of the assembly housing, the air circulating fan including the electric motor that rotates the fan blades; the airflow chamber intake opening; the wick supplied evaporative cooling pad; and the activated charcoal filter element.

With reference to FIG. 5, electrical contact surfaces 72 of assembly housing 18 are wired through conducting cables 84 to pivoting air circulating assembly (FIG. 2). On/off switch 26 (FIG. 2) is a conventional pivotally actuated contact switch. Filter element 56 is positioned between discharge airflow opening 48 and evaporative cooling pad 56. Evaporative cooling pad 56 is positioned between airflow chamber intake opening 46 and filter element 54. With general reference to FIGS. 1–5, operation of welding helmet with air circulating system 10 is as previously described.

It can be seen from the preceding description that a welding helmet with an air circulating system has been provided that has a mechanism for cooling the air prior to circulating the air onto a welder's face; that includes an air filtering mechanism that filters the air to remove particles and unpleasant odors from the air prior to circulating the air onto a welder's face; and that includes a welding hood, a head band assembly, and an air circulating system; the welding hood having an interior face receiving cavity defined by an interior helmet surface; the head band assembly being pivotally mounted to the welding helmet; the air circulating system including an air circulating assembly mounted to a top portion of the welding hood, a cooling water storage bottle attached to a back portion of the head band, a wick conduit connected between the air circulating assembly and the cooling water storage bottle, a detachable battery pack housing mountable to a front structure of the air cooling assembly, and a pivotally actuated air circulating assembly on/off switch mounted between the welding hood and the head band; the battery pack housing having a battery provided therein and a pair of contact pads on a battery pack exterior surface thereof; the air circulating assembly including: an assembly housing mounted to the exterior top portion of the welding hood; a discharge airflow opening formed between an interior airflow chamber of the assembly housing and the interior face receiving cavity of the welding hood; an air circulating fan housed within the airflow chamber of the assembly housing having an electric motor that rotates a number of fan blades to draw air through the airflow chamber intake opening, across an evaporative cooling pad positioned within the airflow chamber, through an activated charcoal filter element positioned within the airflow chamber, and out through the discharge airflow opening into the interior face receiving cavity of the welding hood to provide cool, clean air to a user; the evaporative cooling pad being a fibrous pad supplied with water from the cooling water storage bottle by a wick positioned through the wick conduit.

It is noted that the embodiment of the welding helmet with an air circulating system described herein in detail for exemplary purposes is of course subject to many different variations in structure, design, application and methodology. Because many varying and different embodiments may be made within the scope of the inventive concept(s) herein taught, and because many modifications may be mace in the embodiment herein detailed in accordance with the descriptive requirements of the law, it is to be understood that the details herein are to be interpreted as illustrative and not in a limiting sense.

What is claimed is:

1. A welding helmet with air circulating system comprising:
    a welding hood;
    a head band assembly; and
    an air circulating system;
    said welding hood having an interior face receiving cavity defined by an interior helmet surface;
    said head band assembly being pivotally mounted to said welding helmet;
    said air circulating system including:
        an air circulating assembly mounted to a top portion of said welding hood,
        a cooling water storage bottle attached to a back portion of said head band,
        a wick conduit connected between said air circulating assembly and said cooling water storage bottle,
        a detachable battery pack housing mountable to a front structure of said air cooling assembly, and
        a pivotally actuated air circulating assembly on/off switch mounted between said welding hood and said head band;
    said battery pack housing having a pair of contact pads on a battery pack exterior surface thereof;
    said air circulating assembly including:
        an assembly housing mounted to said exterior top portion of said welding hood;
        a discharge airflow opening formed between an interior airflow chamber of said assembly housing and said interior face receiving cavity of said welding hood;
        an air circulating fan housed within said airflow chamber of said assembly housing having an electric motor that rotates a number of fan blades to draw air through an airflow chamber intake opening, across an evaporative cooling pad positioned within said airflow chamber, through a filter element positioned within said airflow chamber, and out through said discharge airflow opening into said interior face receiving cavity of said welding hood to provide cool, clean air to a user.

2. The welding helmet with air circulating system of claim 1, wherein:
    said filter element is an activated charcoal filter.

3. The welding helmet with air circulating system of claim 1, wherein:
    said filter element is positioned between said discharge airflow opening and said evaporative cooling pad.

4. The welding helmet with air circulating system of claim 1, wherein:
    said evaporative cooling pad is a fibrous pad supplied with water from said cooling water storage bottle by a wick positioned through said wick conduit.

5. The welding helmet with air circulating system of claim 1 wherein:
    said assembly housing includes a pivotable top closure member that pivots to provide sufficient access into said airflow chamber to allow insertion and removal of said filter element into said airflow chamber.

6. The welding helmet with air circulating system of claim 1 wherein:
    said evaporative cooling pad is positioned between said airflow chamber intake opening and said filter element positioned within said airflow chamber.

7. The welding helmet with air circulating system of claim 2, wherein:
    said filter element is positioned between said discharge airflow opening and said evaporative cooling pad.

8. The welding helmet with air circulating system of claim 2, wherein:
    said evaporative cooling pad is a fibrous pad supplied with water from said cooling water storage bottle by a wick positioned through said wick conduit.

9. The welding helmet with air circulating system of claim 2 wherein:
    said assembly housing includes a pivotable top closure member that pivots to provide sufficient access into said airflow chamber to allow insertion and removal of said filter element into said airflow chamber.

10. The welding helmet with air circulating system of claim 2 wherein:

said evaporative cooling pad is positioned between said airflow chamber intake opening and said filter element positioned within said airflow chamber.

11. The welding helmet with air circulating system of claim 7, wherein:

said evaporative cooling pad is a fibrous pad supplied with water from said cooling water storage bottle by a wick positioned through said wick conduit.

12. The welding helmet with air circulating system of claim 7 wherein:

said assembly housing includes a pivotable top closure member that pivots to provide sufficient access into said airflow chamber to allow insertion and removal of said filter element into said airflow chamber.

13. The welding helmet with air circulating system of claim 7 wherein:

said evaporative cooling pad is positioned between said airflow chamber intake opening and said filter element positioned within said airflow chamber.

14. The welding helmet with air circulating system of claim 11 wherein:

said assembly housing includes a pivotable top closure member that pivots to provide sufficient access into said airflow chamber to allow insertion and removal of said filter element into said airflow chamber.

15. The welding helmet with air circulating system of claim 11 wherein:

said evaporative cooling pad is positioned between said airflow chamber intake opening and said filter element positioned within said airflow chamber.

16. The welding helmet with air circulating system of claim 14 wherein:

said evaporative cooling pad is positioned between said airflow chamber intake opening and said filter element positioned within said airflow chamber.

17. The welding helmet with air circulating system of claim 3, wherein:

said evaporative cooling pad is a fibrous pad supplied with water from said cooling water storage bottle by a wick positioned through said wick conduit.

18. The welding helmet with air circulating system of claim 3 wherein:

said assembly housing includes a pivotable top closure member that pivots to provide sufficient access into said airflow chamber to allow insertion and removal of said filter element into said airflow chamber.

19. The welding helmet with air circulating system of claim 3 wherein:

said evaporative cooling pad is positioned between said airflow chamber intake opening and said filter element positioned within said airflow chamber.

* * * * *